United States Patent [19]

Fulwyler

[11] 4,095,898
[45] Jun. 20, 1978

[54] PARTICLE ANALYSIS SYSTEM WITH PHOTOCHROMIC FILTER

[75] Inventor: Mack J. Fulwyler, Los Alamos, N. Mex.

[73] Assignee: Coulter Electronics, Inc., Hialeah, Fla.

[21] Appl. No.: 694,531

[22] Filed: Jun. 10, 1976

[51] Int. Cl.² .............. G01N 21/00; G01N 15/02; G02B 5/23
[52] U.S. Cl. .................... 356/103; 356/102; 350/357
[58] Field of Search ............... 356/102, 103, 39, 104; 350/311, 314, 160 R, 160 P

[56] References Cited

U.S. PATENT DOCUMENTS

| | | | |
|---|---|---|---|
| 3,208,860 | 9/1965 | Armistead | 350/160 P |
| 3,703,388 | 11/1972 | Araujo | 350/160 P |
| 3,705,771 | 12/1972 | Friedman | 356/104 |
| 3,710,933 | 1/1973 | Fulwyler | 356/39 |
| 3,714,430 | 1/1973 | Finvold | 350/160 P |
| 3,716,747 | 2/1973 | Patel | 350/160 P |
| 3,781,112 | 12/1973 | Groner | 356/104 |
| 3,893,767 | 7/1975 | Fulwyler | 356/39 |

*Primary Examiner*—Samuel W. Engle
*Assistant Examiner*—Donald P. Walsh
*Attorney, Agent, or Firm*—Silverman, Cass & Singer Ltd.

[57] ABSTRACT

A background light filter for use in an optical particle analysis system operates to attenuate light coupled thereto and pass an attenuated intensity light signal. If the light coupled to the filter takes the form of discrete beams or areas forming a pattern, the filter will selectively attenuate in only those portions of the filter struck by the light beams forming the pattern. The optical filter is substantially insensitive to short term variations in light coupled thereto so that changes in the received light pattern which may, for example, be produced by passage of a particle through the light beam producing the pattern, will be passed through the optical filter with substantially no attenuation.

1 Claim, 2 Drawing Figures

PARTICLE ANALYSIS SYSTEM WITH PHOTOCHROMIC FILTER

BACKGROUND OF THE INVENTION

The present invention relates to photoanalysis apparatus and more particularly to photoresponsive apparatus for detecting various characteristics of small particles such as blood cells.

There is a great need for accurate analysis of the characteristics of groups of small particles. A particularly important field for such analysis is in medical research and diagnosis where, for example, blood cells and other biological cells must be analyzed.

Various systems have been developed for analyzing groups of small particles such as blood cells. In one system the analysis is accomplished optically by entraining the particles such as blood cells in a very thin stream of liquid and passing the stream containing the particles through an optical scanning station. A photo-optical detecting device is arranged to detect the optical reaction of each particle to illumination from a beam of light.

In photoanalysis systems as described above it has been recognized that the light scattering effect and the fluorescent effect produced by particles in the stream passing through the optical scanning station varies according to different characteristics of the particles, including such factors as particle size, refractive index, particle staining and composition. It has also been found that the beam of light passing through the liquid stream forms a light pattern, the light pattern being different for the stream with and without particles as well as for different size and type particles. Additionally, the thin stream of liquid produces light reflections at various interfaces such as the air/water or glass/water interface. The reflections, light pattern and light beam all are coupled to a photodetector which converts the light signals received to electrical signals which are analyzed to determine presence of a particle and particle characteristics.

The light pattern and light reflections developed at the photodetector when no particle passes through the light beam may have a rather high intensity. This high intensity light will create noise in the electrical signals produced by the photodetector. To eliminate the noise the photodetector sensitivity may be decreased.

The variation in the light reflection and light pattern formed at the detector in response to passage of a particle through the light beam may not be very great so that the resultant variation and electrical output signal from the photodetector may be small. Because of the high noise level due to the background light and the reduced photodetector sensitivity, it may be difficult to detect particles or to accurately detect and identify various particle characteristics. It is therefore desirable to eliminate or minimize, to the greatest extent possible, the light patterns and light reflections received by the photodetector when there are no particles in the flow stream passing through the light beam. That is, to minimize the background light.

SUMMARY OF THE INVENTION

In practicing this invention, a particle analysis system is provided wherein a light beam is passed through a fluid stream to a photodetector. The light beam passing through the stream produces light reflections and a light pattern. Passage of a particle through the fluid stream and through the light beam varies the amount and intensity of light passing through the fluid stream, the reflected light and the light pattern. In the system, a background light filter is positioned between the fluid stream and a photodetector. The filter operates in response to the light reflections and the light patterns received thereat to slowly increase in optical density at the points the light pattern strikes the filter and attenuate the pattern passing through the filter to the photodetector. The filter is substantially insensitive to rapid changes in the light pattern produced, for example, by passage of a particle in the fluid stream through the light beam so that the light variations resulting from particle passage will pass through the filter to the photodetector allowing particle detection and analysis.

Figure 1:
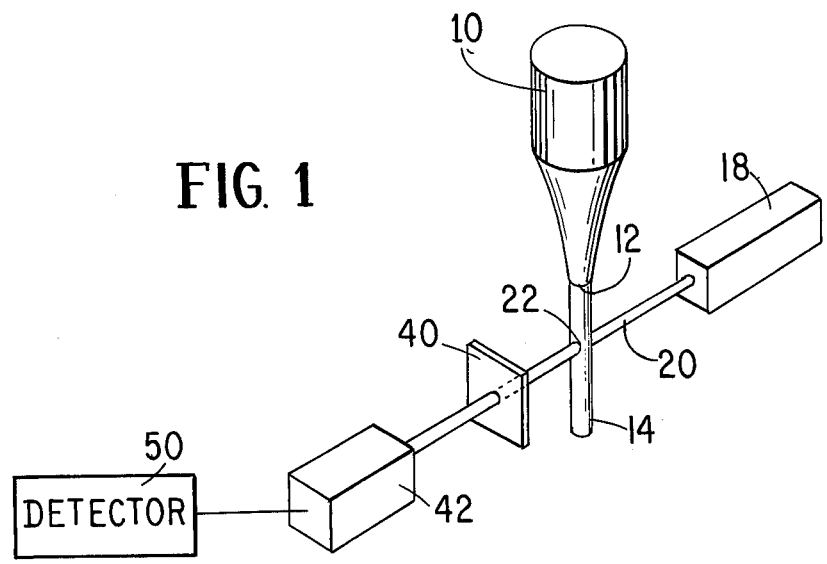
FIG. 1 is a simplified perspective drawing of one embodiment of the apparatus of this invention.

DETAILED DISCUSSION OF THE PREFERRED EMBODIMENTS:

Referring to FIG. 1, there is shown a photoanalysis system including a container 10 for storing a fluid containing particulate matter to be analyzed. It is to be understood that container 10 may include all necessary pressurizing and pressure regulating apparatus for causing the fluid to exit container 10 continuously at a prescribed flow rate.

In operation, the fluid in container 10 exits via orifice 12 and forms a fluid column which flows downward. A light source 18, which in the preferred embodiment is a laser, produces a laser beam 20 which intersects the fluid column 14 at a first location 22.

Figure 2:
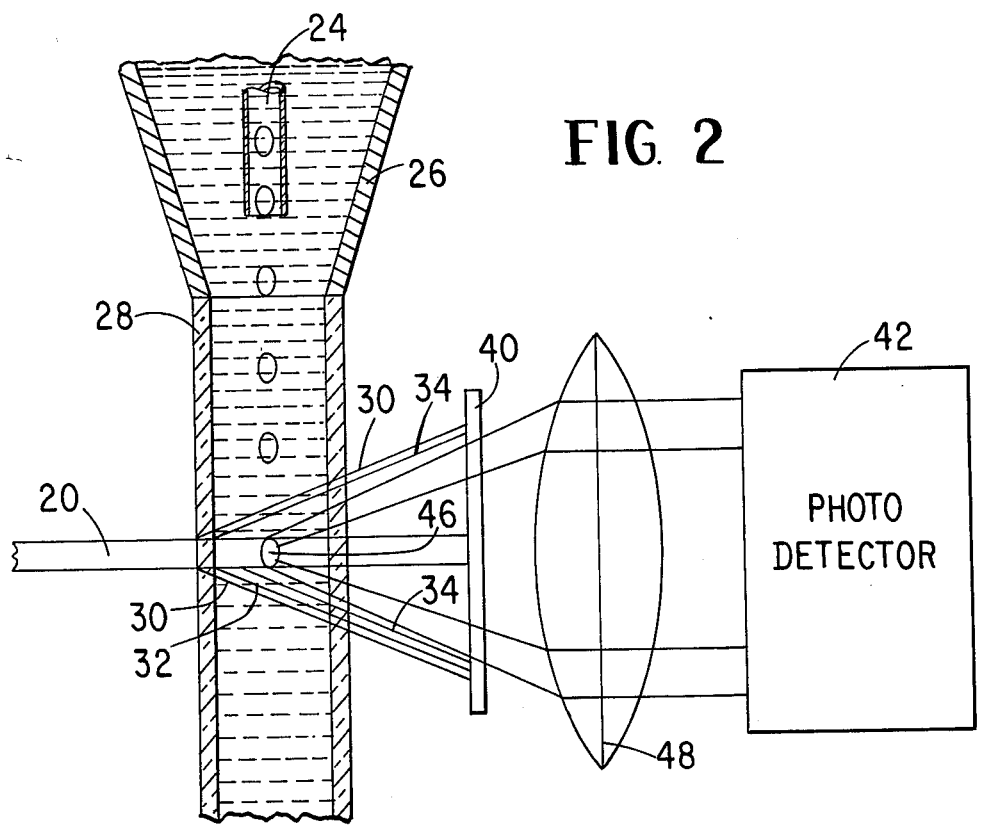
FIG. 2 is a cutaway plan view of a portion of another embodiment of the apparatus of this invention.

Referring now to FIG. 2, there is shown a somewhat different apparatus configuration wherein particle laden fluid from a container 10 is coupled to and out of an inner nozzle 24 and a particle free sheath liquid is coupled to and through an outer nozzle 26. Details of such a structure may be found in U.S. Pat. No. 3,710,933. In the aforementioned structure, the particle containing fluid is entrained in the center of the flowing stream of sheath fluid, and in FIG. 2, the following stream is passed through an optical chamber 28. Optical chamber 28 is formed from a highly light transmissive medium such as glass or plastic. In the embodiment shown in FIG. 2, light beam 20 from laser 18 is passed to and through optical chamber 28 and the fluid contained therein. Light beam 20 also strikes and passes through fluid column 14 shown in FIG. 1. In the embodiment of FIG. 2, the glass air interface at the outer surface of optical chamber 28 will produce light reflections represented by a light beam 30. The interface between the fluid stream and the wall of optical chamber 28 also creates a reflected light beam represented by beam 32. Turbulence in the fluid stream also causes reflections and one such beam 34 is identified. In addition to the noted reflected light beams, the passage of the beam 20 through the fluid stream itself can produce a distinct light pattern. The reflected light beams identified, the light pattern produced by passage of light beam 20 through optical chamber 28 and light beam 20 itself all pass to a background light filter 40. In FIG. 1 the air water interface and fluid turbulence produce reflections, which along with the light pattern, pass to filter 40.

Filter 40 is a structure which has a variable light attenuation characteristic. More specifically, the light attenuation of optical filter 40 will increase slowly or the light transmission will decrease slowly in response to a light beam or light pattern striking the filter. The attenuation increase and transmission decrease will only occur at the specific locations on filter 40 where the beam or pattern strikes. For example, in FIG. 2, the light attenuation of filter 40 will increase only at the points where the light beams 30, 32 and 34 strike the filter. Although it is not shown in FIG. 2, it should be understood that the light pattern formed by the intersection of flow stream and light beam 20 will also cause attenuation of filter 40, only at the location on filter 40 struck by the pattern. The amount of attenuation provided by filter 40, at the noted locations, is dependent upon the length and intensity of the light striking the filter and the material used for the filter itself. At least during the time that no particle passes through the light beam then, photodetector 42 will receive substantially no light. Because very little if any light is received at photodetector 42 the gain of photodetector 42 may be set at a maximum level without concern for a high ambient noise level normally produced by a high ambient light level reaching detector 42.

In the preferred embodiment, filter 40 takes the form of a photochromic mechanism. The reaction in filter 40 is similar to that which takes place when light strikes the emulsions of many photographic films containing silver halides. However, when the film is developed, the darkened image is permanently fixed whereas with the photochromic filter of the instant invention, the darkening and attenuating process is completely reversible depending upon the amount and intensity of light present.

The preferred form of photochromic mechanism used for background light filter 40 is a photochromic glass such as is presently manufactured and sold by the Corning Glass Works of Corning, N.Y. under the trademarks "PHOTOGRAY" or "SUNGRAY".

When a particle such as particle 46, shown in FIG. 2, passes through light beam 20, it will create a light pattern different from the light pattern present when no particle is present. This pattern will be created for only a very short time period, specifically the time period that particle 46 passes through beam 20. The light pattern created is coupled to filter 40. As previously mentioned, filter 40 slowly increases in light attenuation and decreases in light transmissivity in response to received light so that any variation in received light which occurs quickly and for a short time period, will not affect the existing attenuation characteristics of filter 40. Consequently, the light pattern produced by the passage of particle 46 will pass through filter 46 substantially unattenuated. In FIG. 2 the light pattern passes to a converging lens 48 which operates to focus the beams forming the light pattern to photodetector 42. In FIG. 1, the light beams passed by filter 40 proceed directly to photodetector 42. Photodetector 42 receives the light pattern and develops electrical signals in response to the light pattern which are coupled to a detector 50. Because of the high sensitivity of photodetector 42, a substantially greater amount of the light pattern received at detector 42 can be converted to electrical signals and coupled to detector 50. The additional information provided by the additionally detected signals may be employed for identifying additional characteristics of the particle, which characteristics were not previously identifiable because of the high ambient light level.

While the present invention has been described by reference to specific examples, it is to be understood that modifications may be made by those skilled in the art without actually departing from the invention shown and described herein. It is therefore intended that the appended claims cover all variations that fall within the scope and spirit of this invention.

What is desired to be secured by Letters Patent of the United States is:

1. A particle analysis system including in combination;

means for forming a flow stream containing particles to be detected, a source of light for producing a light beam, means for directing said light beam through said flow stream at a first location in a first direction, said light beam passing through said flow stream producing light reflections and a light pattern, said light pattern, light reflection and light beam passing through said flow stream varying rapidly and for a short time period in response to passage of a particle through said first location, a background light filter aligned with said light beam for receiving said light beam passed through said flow stream and for receiving said light pattern and light reflections, said background light filter being operative to slowly increase in optical density at the points thereon where said light pattern light beam and light reflections strike said filter and attenuate said light pattern, light beam and light reflections as they pass through said filter in said first direction, said filter being substantially insensitive to said rapid, short time period variations in said light pattern, light reflections and light beam for passing said variations through said filter in said first direction substantially unattenuated, said filter including a photochromic transparent medium, photodetector means for receiving said light beam, light pattern and light reflections passed through said filter in said first direction, said photodetector means operative to develop signals which vary in accordance with variations in said light reflections, light pattern and the light beam received thereat, and detection means coupled to said photodetector means and operative in response to said signal variations to detect said particle.

* * * * *